US010420942B1

United States Patent
Eubanks

(10) Patent No.: US 10,420,942 B1
(45) Date of Patent: Sep. 24, 2019

(54) PATIENT-INITIATED AUTOMATIC CONTROL OF NEURAL TISSUES

(71) Applicant: Thomas M Eubanks, Edinburg, TX (US)

(72) Inventor: Thomas M Eubanks, Edinburg, TX (US)

( * ) Notice: Subject to any disclaimer, the term of this patent is extended or adjusted under 35 U.S.C. 154(b) by 0 days.

(21) Appl. No.: 16/140,277

(22) Filed: Sep. 24, 2018

Related U.S. Application Data

(63) Continuation of application No. 15/808,128, filed on Nov. 9, 2017, now Pat. No. 10,118,039.

(51) Int. Cl.
*A61N 1/36* (2006.01)
*A61N 1/372* (2006.01)
*A61N 1/05* (2006.01)

(52) U.S. Cl.
CPC ....... *A61N 1/36139* (2013.01); *A61N 1/0531* (2013.01); *A61N 1/36067* (2013.01); *A61N 1/36103* (2013.01); *A61N 1/37247* (2013.01)

(58) Field of Classification Search
CPC ............ A61N 1/36139; A61N 1/36067; A61N 1/37247; A61N 1/0531; A61N 1/36103
See application file for complete search history.

(56) References Cited

U.S. PATENT DOCUMENTS

2017/0281086 A1* 10/2017 Donaldson ........... A61B 5/6803

* cited by examiner

*Primary Examiner* — Rex R Holmes
(74) *Attorney, Agent, or Firm* — Plager Schack LLP

(57) ABSTRACT

A patient-initiated automatic neural tissue control system and methods of providing patient-initiated automatic control of neural tissues are disclosed. The patient-initiated automatic neural tissue control system and methods allow for patient-defined internal initiation of motor control, by initiation of the controlling signals in the contralateral motor area the patient controls (e.g., previously damaged motor areas). The patient-initiated automatic neural tissue control system and methods involve brain signals that initiate from patient-defined motor actions from the contralateral motor area of the patient's brain which stimulates brain areas near the damaged brain areas. The brain areas stimulated near the damaged brain area include brain areas adjacent to the damaged brain area and brain areas below the damaged brain area.

4 Claims, 4 Drawing Sheets

US 10,420,942 B1

PATIENT-INITIATED AUTOMATIC CONTROL OF NEURAL TISSUES

CLAIM OF BENEFIT TO PRIOR APPLICATION

This application is a continuation of and claims benefit to U.S. Non-Provisional patent application Ser. No. 15/808,128, entitled "PATIENT-INITIATED AUTOMATIC CONTROL OF NEURAL TISSUES." filed Nov. 9, 2017, and now issued as U.S. Pat. No. 10,118,039. The U.S. Non-Provisional patent application Ser. No. 15/808,128, now U.S. Pat. No. 10,118,039, is incorporated herein by reference.

BACKGROUND

Embodiments of the invention described in this specification relate generally to neural tissue stimulation and control, and more particularly, to a system and method of providing patient-initiated automatic control of neural tissues.

Brain injuries can arise from any number of events or situations, such as stroke or impact-related traumatic brain injuries. People who suffer from brain injuries typically are treated at medical facilities which limit ongoing damage to brain tissue. However, such brain injured people (hereinafter referred to as "patients") are often left with traumatic brain injuries that limit the patient's ability to control motor functions of body parts (e.g., limbs, fingers, etc.) associated with neural tissue in the damaged brain area.

While various existing direct brain stimulation methods are capable of stimulating the brain with electrical impulses (e.g., using implanted electrodes) to treat a variety of brain conditions (e.g., major depressive disorder, Parkinson's disease, strokes, essential tremors, tremors arising from multiple sclerosis, etc.), there are no existing systems or methods, to date, which provide a patient-initiated locus of control as a work-around to restore body motor functions which, until the occurrence of brain injury, were controlled by the damaged neural areas of the brain.

Conventional system and traditional methods of direct brain stimulation generally involve surgically implanting electrodes within the brain to then externally operate the electrodes (e.g., by applying a current to the electrode using an insulated conductor) to deliver electrical impulses capable of counteracting certain electrical activities in the brain, and in particular the abnormal activity believed to cause undesirable conditions and symptoms, such as those brain conditions identified above. Noninvasive techniques such as transcranial magnetic and direct current stimulation have been developed but provide transient and little if any long term value.

Some existing conventional systems monitor brain activity for desired activity and stimulate the pleasure centers to try to induce or shape further increases in brain activity in coma patients.

Some existing methods and conventional systems use adaptive brain stimulation, which is based upon three components: stimulation, comparison of a present state with a reference state, and subsequent stimulation that is contingent upon the results of the comparison. Still another conventional technique seeks to maintain stasis of base brain frequencies to prevent seizures by monitoring activity and applying stimulating current to maintain normal activity levels. However, the existing systems and methods neither involve voluntary patient control nor define control by comparing voluntary patient neural output to previously recorded voluntary motor neural activity to trigger processor control and initiate a sequence of stimulation that would cause previously damaged areas to regain function.

However, all of the existing systems and methods rely on an external source or processor control to initiate stimulation and fail to provide for the initiation of the stimulation signal that comes from a patient-determined voluntary motor action. Thus, among the existing methods, none allow for internal initiation which will move to repair and create new connections. As such, many patients have no way to regain any patient-initiated functional control from losses suffered by their brain injuries.

Therefore, what is needed is a way to provide patient-initiated automatic control of neural tissues.

BRIEF DESCRIPTION

A novel patient-initiated automatic neural tissue control system and methods for controlling bodily motor functions by stimulating healthy neural tissues to compensate for damaged neural tissues naturally associated with the bodily motor functions are disclosed.

In some embodiments, the patient-initiated automatic neural tissue control system includes a micro processor comprising an input-output (I/O) board and a transceiver unit for transmission and reception of signals arising from neural tissues. In some embodiments, the patient-initiated automatic neural tissue control system includes a power supply that provides electric power to the micro processor, the I/O board, and the transceiver unit. In some embodiments, the patient-initiated automatic neural tissue control system includes a programming interface which is used for a program that automatically controls neural tissues when the program is executing on the micro processor.

In some embodiments, the micro processor is secured to the patient. In some embodiments, the micro processor performs processor control to record voluntary neural activity with multiplexed electrodes in a functioning area of a brain and is configured to compare voluntary neural activity to previously generated voluntary action recordings. In some embodiments, motor control near damaged neural tissue is stimulated by the micro processor to allow for contralateral neural stimulation near damaged areas based on initiation from predefined patient defined motor activity. In some embodiments, the micro processor is programmed with initiation triggers and contralateral stimulating parameters, defined by the patient via the programming interface, and sequences in the processor control. In some embodiments, the patient-initiated automatic neural tissue control system is actuated by one or more patient defined motor sequences. In some embodiments, signals initiate from patient defined motor actions, or sequences, from the contralateral motor area, and once initiated, the signals stimulate areas adjacent to or below damaged areas of the patient's brain.

In some embodiments, the methods for controlling bodily motor functions by stimulating healthy neural tissues to compensate for damaged neural tissues naturally associated with the bodily motor functions include a method of providing patient-initiated automatic control of neural tissues.

In some embodiments, the method of providing patient-initiated automatic control of neural tissues includes implantation of multiplexed electrodes in functioning motor cortex and phased array electrodes close to the damaged neural tissue. In some embodiments, the method of providing patient-initiated automatic control of neural tissues allows for patient-defined internal initiation of motor control, by initiation of the controlling signals in the contralateral motor area the patient controls (e.g., previously damaged motor areas). In some embodiments, the method of providing patient-initiated automatic control of neural tissues involves brain signals that initiate from patient-defined motor actions from the contralateral motor area of the patient's brain which stimulates brain areas near the damaged brain areas. In some embodiments, the brain areas stimulated near the damaged brain area include brain areas adjacent to the damaged brain area and brain areas below the damaged brain area.

In some embodiments, the methods for controlling bodily motor functions by stimulating healthy neural tissues to compensate for damaged neural tissues naturally associated with the bodily motor functions include a method for automatically controlling neural tissues.

In some embodiments, the method for automatically controlling neural tissues includes a method for recording a patient defined on-off toggle from a motor action or sequence to set an operation mode of the processor control to one of active and standby. In some embodiments, the process control captures initiation triggers and contralateral stimulating parameters when the operation mode of the processor control is set to active. In some embodiments, the process control ignores initiation triggers and contralateral stimulating parameters when the operation mode of the processor control is set to standby. In this way, the patient can reliably perform motor actions to stimulate neural tissues when the patient intends to do so (i.e., in active mode), while ensuring that the same motor actions do not inadvertently trigger initiation of neural tissue stimulation when the patient does not intend to (i.e., in standby mode).

In some embodiments, the method for automatically controlling neural tissues includes a method for training a patient to perform a sequence of motor actions to trigger initiation of neural tissue stimulation. In this way, the patient can improve the accuracy and speed of performing the patient defined motor sequences to reliably trigger stimulation of the corresponding neural tissue areas of the brain.

In some embodiments, the method for automatically controlling neural tissues includes a method for sending appropriate neural tissue stimulation to trigger a motor activity of a patient by monitoring and matching neural activity corresponding to a patient motor sequence to stored motor sequence neural activity that triggers stimulation of the appropriate neural tissue. In this way, the patient can affect motor movement sequences, which would normally correspond to neural tissue areas of the brain which have been damaged, by performing a compensating motor sequence defined to initiate stimulation of the neural tissue.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
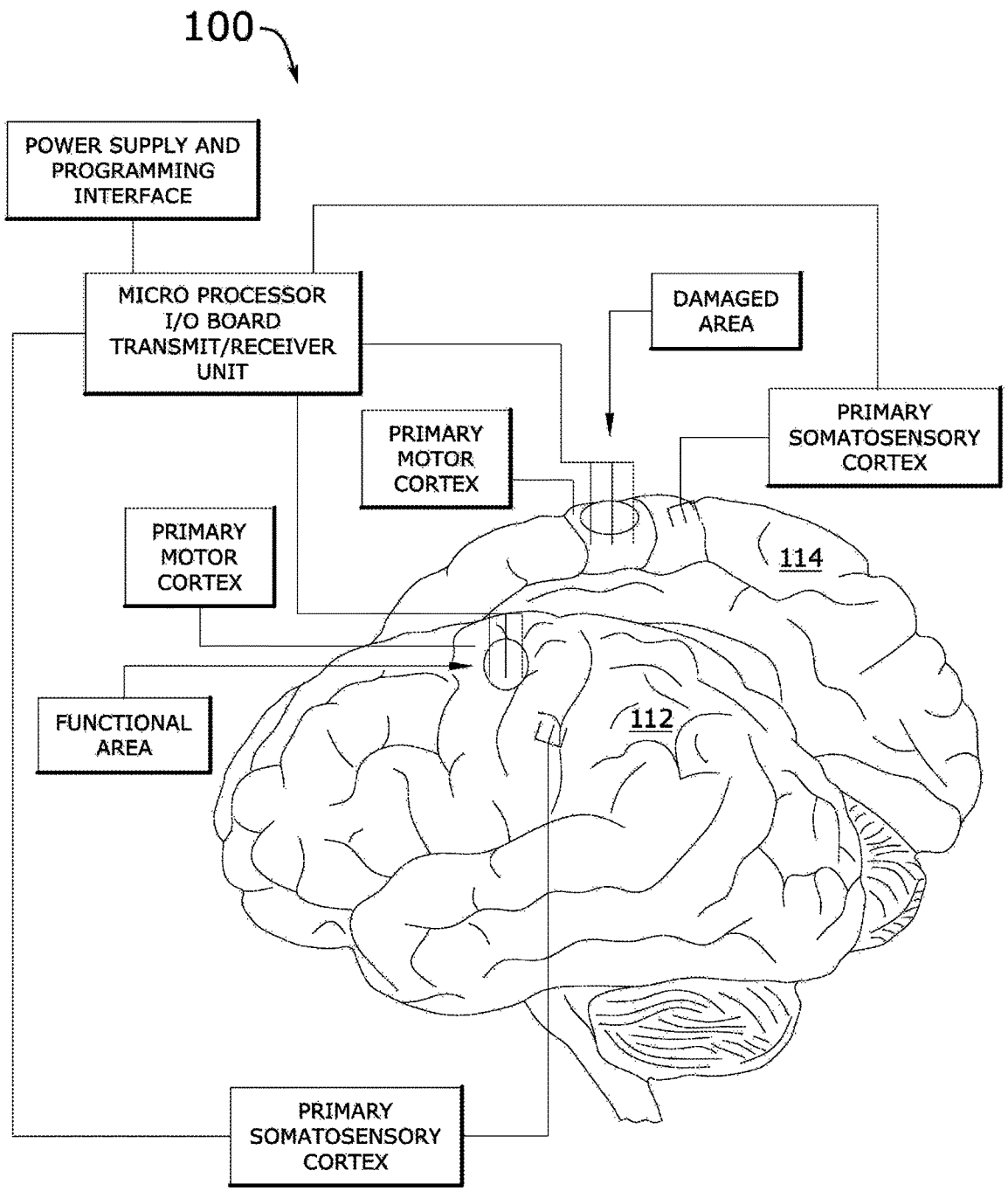
FIG. 1 conceptually illustrates a schematic perspective view of the brain stimulation methods shown in use by a patient-initiated automatic neural tissue control system in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel patient-initiated automatic neural tissue control system and methods for controlling bodily motor functions by stimulating healthy neural tissues to compensate for damaged neural tissues naturally associated with the bodily motor functions. In some embodiments, the methods for controlling bodily motor functions by stimulating healthy neural tissues to compensate for damaged neural tissues naturally associated with the bodily motor functions include a method of providing patient-initiated automatic control of neural tissues. In some embodiments, the methods for controlling bodily motor functions by stimulating healthy neural tissues to compensate for damaged neural tissues naturally associated with the bodily motor functions include a method for automatically controlling neural tissues.

In some embodiments, the patient-initiated automatic neural tissue control system and methods allow for patient-defined internal initiation of motor control, by initiation of the controlling signals in the contralateral motor area the patient controls (e.g., previously damaged motor areas). In some embodiments, the patient-initiated automatic neural tissue control system and methods involve brain signals that initiate from patient-defined motor actions from the contralateral motor area of the patient's brain which stimulates brain areas near the damaged brain areas. In some embodiments, the brain areas stimulated near the damaged brain area include brain areas adjacent to the damaged brain area and brain areas below the damaged brain area.

In some embodiments, the method of providing patient-initiated automatic control of neural tissues includes implantation of multiplexed electrodes in functioning motor cortex and phased array electrodes close to the damaged neural tissue. In some embodiments, the method of providing patient-initiated automatic control of neural tissues allows for patient-defined internal initiation of motor control, by initiation of the controlling signals in the contralateral motor area the patient controls (e.g., previously damaged motor areas). In some embodiments, the method of providing patient-initiated automatic control of neural tissues involves brain signals that initiate from patient-defined motor actions from the contralateral motor area of the patient's brain which stimulates brain areas near the damaged brain areas. In some embodiments, the brain areas stimulated near the damaged brain area include brain areas adjacent to the damaged brain area and brain areas below the damaged brain area.

As stated above, traumatic brain injury, stroke, and other brain damage typically results in damaged neural tissues in the brain which limit a patient's ability to control motor functions of body parts (e.g., limbs, fingers, etc.) associated with damaged neural tissues. While there are several existing direct or adaptive brain stimulation or other techniques, systems, and methods used to provide a level of functional control, all of the existing options rely on an external source or processor control to initiate stimulation and fail to provide for the initiation of the stimulation signal that comes from a patient-determined voluntary motor action. Thus, among the existing methods, none allow for internal initiation which will move to repair and create new connections. As such, many patients have no way to regain any patient-initiated functional control from losses suffered by their brain injuries.

Embodiments of the patient-initiated automatic neural tissue control system and methods described in this specification solve such problems by using functional neural tissue to initiate a sequence of controlling signals initiated by voluntary patient neural output. In some embodiments, an electronic system or an electronic device to conduct this kind of neural control can be controlled externally or with radio frequency magnetic field induction and can be completely implantable in the patient. There are several companies that manufacture alternatives, such as a device similar to a cochlear implant system. For example, Sensory Systems Inc. makes a micro miniature stimulation device that has not been configured to trigger from a recognition processor recording array. These systems do not involve voluntary patient control or define control by comparing voluntary patient neural output to previously recorded voluntary motor neural activity for the purpose of triggering processor control and initiate a sequence of stimulation that would cause previously damaged areas to regain motor control. The present patient-initiated automatic neural tissue control system and methods teaches patient control that allows for enabling or disabling the patient-initiated automatic neural tissue control system through the use of patient defined motor activity. For example, the patient can define a motor sequence to toggle between an active mode in which the patient-initiated automatic neural tissue control system monitors and triggers stimulation of neural tissue for matching motor sequences and a standby mode in which motor activities do not trigger stimulation of neural tissue. In other words, by using a patient defined motor sequence, the patient can turn the patient-initiated automatic neural tissue control system off so they can use the patient defined motor pathways without triggering control of the damaged areas (e.g., so the patient can move a left arm as desired without that patient's right leg trying to walk). Furthermore, the present patient-initiated automatic neural tissue control system and methods use specific agents that encourage the creation of new neural connections. For example, the patient-initiated automatic neural tissue control system and methods of some embodiments can be used together with Reneuron's CTX stem cell therapy, which significantly improves damage from stroke or traumatic brain injury (TBI) by injection of the CTX stem cell agent into the damaged areas of the brain, and which in combination with the present patient-initiated automatic neural tissue control system and methods, may improve new neural connections through the surrounding brain area with patient-directed neural activity, and may also improve on new neural connections in the hippocampus and other midbrain structures associated with motor learning.

In some embodiments, the patient-initiated automatic neural tissue control system and methods allow for a variable tolerance in what is accepted as an initiating trigger, so that if a recorded signal is within range of what produces an acceptable outcome it is added to the database of initiating triggers, and weighted so that smaller and smaller initiating signals are accepted as triggers to the sequence of stimulating currents that are required to initiate motor control in previous damaged areas.

In some embodiments, the patient-initiated automatic neural tissue control system and methods provide at least one of external and implantable recognition processor control of a plurality of electrodes recording electrical signals produced by voluntary patient-defined realtime neural activity which are matched against the patient-defined electrical recorded (and stored) signals and the recognition processors controlling one or more interruptible initiation signals of the stimulating electrode array processor positioned under or adjacent to damaged areas of neural tissue. In some embodiments, one or more of these processors are pattern recognition processors capable of recording and storing, in a database, the patient-defined electrical signals generated by patient-conscience motor control and comparing the recordings to a plurality of previously recorded and stored electrical signals produced by voluntary functional neural activity in a contralateral motor area. In some embodiments, further control of the processors to accept, reject, or prioritize and then actuate a plurality of initiation triggers controlling the output sequence and location of stimulating current may be applied to areas adjacent to or below damaged neural tissue by a plurality of electrode systems. Recognition processor control by means of implanted or external remote control by one or more electrode arrays placed in a sensory motor area related to the damaged area that will also provide control to accept, reject or prioritize recorded signals in the data set as triggers to the stimulating output electrode arrays would allow for new signals to be added to the database of initiating triggers generated by patient-defined voluntary realtime motor cortex neural activity.

Some embodiments of the patient-initiated automatic neural tissue control system teach a method of patient control that allows for turning the patient-initiated automatic neural tissue control system on and off by the use of patient-defined motor activity. By using a patient defined motor sequence, the patient can turn the patient-initiated automatic neural tissue control system off so that they can use the patient-defined motor pathways without triggering control of the damaged areas. Basically, this allows the patient to be able to move his or her left arm around without triggering movement in your right leg, when such is the patient-defined voluntary realtime motor cortex neural activity.

In some embodiments, the method for the automatic control of neural tissues includes implantation of multiplexed electrodes in functioning motor cortex and phased array electrodes close to the damaged neural tissue. In some embodiments, a processor control to record voluntary neural activity with multiplexed electrodes in a functioning area configured to compare voluntary neural activity to previously generated voluntary action recordings is secured to the subject. In some embodiments, motor control near damaged neural tissue is stimulated by the processor to allow for contralateral neural stimulation near damaged areas based on initiation from predefined patient defined motor activity. In some embodiments, the processor is programmed with patient defined initiation triggers and contralateral stimulating parameters and sequences in the processor control. In some embodiments, the patient-initiated automatic neural tissue control system is actuated by a patient defined motor sequence. In some embodiments, signals initiate from patient defined motor actions from the contralateral motor area and stimulates areas adjacent to or below damaged areas.

In some embodiments, the patient-initiated automatic neural tissue control system includes a micro processor comprising an input-output (I/O) board and a transceiver unit for transmission and reception of signals arising from neural tissues. In some embodiments, the patient-initiated automatic neural tissue control system includes a power supply that provides electric power to the micro processor, the I/O board, and the transceiver unit. In some embodiments, the patient-initiated automatic neural tissue control system includes a programming interface which is used for a program that automatically controls neural tissues when the program is executing on the micro processor.

In some embodiments, the micro processor is secured to the patient. In some embodiments, the micro processor performs processor control to record voluntary neural activity with multiplexed electrodes in a functioning area of a brain and is configured to compare voluntary neural activity to previously generated voluntary action recordings. In some embodiments, motor control near damaged neural tissue is stimulated by the micro processor to allow for contralateral neural stimulation near damaged areas based on initiation from predefined patient defined motor activity. In some embodiments, the micro processor is programmed with initiation triggers and contralateral stimulating parameters, defined by the patient via the programming interface, and sequences in the processor control. In some embodiments, the patient-initiated automatic neural tissue control system is actuated by one or more patient defined motor sequences. In some embodiments, signals initiate from patient defined motor actions, or sequences, from the contralateral motor area, and once initiated, the signals stimulate areas adjacent to or below damaged areas of the patient's brain.

By way of example, FIG. 1 conceptually illustrates a schematic perspective view of certain embodiments of the brain stimulation methods shown in use 100. More specifically, FIG. 1 shows a triggering array of implanted electrodes that would be placed on the surface of a user's brain and the inputs to or outputs from would be processed by the patient-initiated automatic neural tissue control system and methods. One triggering array of implanted electrodes are placed on the right hemisphere 112 of the user's brain and another triggering array of implanted electrodes are placed on the left hemisphere 114 of the user's brain. In this way, the patient-initiated automatic neural tissue control system and methods of the present disclosure provides a work around to restore function to damaged neural areas in the brain. In particular, the patient-initiated automatic neural tissue control system and methods provide automatic control between neural tissues that allows for user defined voluntary initiation of motor control, by initiation of the controlling signals in the contralateral motor area the patient controls previously damaged motor areas.

Embodiments of the patient-initiated automatic neural tissue control system and methods described in this specification differ from and improve upon currently existing options. In particular, some embodiments of the patient-initiated automatic neural tissue control system and methods differ because existing systems do not involve voluntary patient control and define control by comparing voluntary patient neural output to previously recorded voluntary motor neural activity to trigger processor control and initiate a sequence of contralateral brain stimulation. In addition, some embodiments of the patient-initiated automatic neural tissue control system and methods improve upon the currently existing options because existing systems utilize external initiation signal strategies. However, when controlling signals come from an external source, those signals do not have a chance of repairing the damage by creating new neural pathways. In contrast, signals that initiate from patient defined motor actions from the contralateral motor area and stimulate areas adjacent to or below damaged areas do so, as is supported by the patient-initiated automatic neural tissue control system and methods of the present disclosure.

The patient-initiated automatic neural tissue control system and methods of the present disclosure may be comprised of the following elements. This list of possible constituent elements is intended to be exemplary only and it is not intended that this list be used to limit the patient-initiated automatic neural tissue control system and methods of the present application to just these elements. Persons having ordinary skill in the art relevant to the present disclosure may understand there to be equivalent elements that may be substituted within the present disclosure without changing the essential function or operation of the patient-initiated automatic neural tissue control system and methods.

1. Multiplexed electrodes are implanted in functioning motor cortex
2. Phased array electrodes are implanted in the brain close to the damaged areas
3. Processor attached to record voluntary neural activity with multiplexed electrodes in functioning area
4. The processor compares the recordings to previously generated voluntary action recordings
5. Stimulate and locate motor control near damaged areas
6. Processor control to allow for contralateral neural stimulation near damaged areas based on initiation from predefined patient defined motor activity
7. System is remotely controlled to program patient defined initiation triggers and contralateral stimulating parameters and sequences
8. One of the previous patient defined motor sequences is used to turn the system on and off The various elements of the patient-initiated automatic neural tissue control system and methods of the present disclosure may be related in the following exemplary fashion. It is not intended to limit the scope or nature of the relationships between the various elements and the following examples are presented as illustrative examples only. The first element (#1—multiplexed electrodes implanted in functioning motor cortex) describes a multiplexed electrode capable of recording neural activity connected to a processor while the second element (#2—phased array electrodes that are implanted in the brain close to the damaged areas) describes a phased array electrode. The patient-initiated automatic neural tissue control system allows for a plurality of neural stimulation focal points, such that the third element (#3—the processor attached to record voluntary neural activity with multiplexed electrodes in functioning area) is attached to the plurality of focal points. The fourth element (#4), the processor which compares the recordings to previously generated voluntary action recordings, also allows connections for programming and control of the patient-initiated automatic neural tissue control system and power supply. In order to stimulate and locate motor control near damaged areas (the fifth element #5), software programming for patient defined activation of stimulating patterns in previously damaged areas is defined. For the sixth element (#6), in which processor control is used to allow for contralateral neural stimulation near damaged areas based on initiation from predefined patient defined motor activity, pattern recognition software allows for operation by patient defined motor activity the patient-initiated automatic neural tissue control system will also allow for a variable tolerance in what is accepted as an initiating trigger, so that if a recorded signal is within range of what produces an acceptable outcome it is added to the data base of initiating triggers weighted so that smaller and smaller initiating signals are accepted as triggers to the sequence of stimulating currents that are required to initiate motor control in previous damaged areas.

The patient-initiated automatic neural tissue control system and methods of the present disclosure generally works as a patient-initiated automatic neural tissue control system and a method of providing automatic control between neural tissues that allows for user defined internal initiation of motor control, which works by initiation of the controlling signals in the contralateral motor area the patient controls previously damaged motor areas. This patient-initiated automatic neural tissue control system teaches a method of patient control that allows for turning the patient-initiated automatic neural tissue control system on and off by the use of patient defined motor activity. By using a patient defined motor sequence, the patient can turn the patient-initiated automatic neural tissue control system off so they can use the patient defined motor pathways without triggering control of the damaged areas.

In some embodiments, the method for automatically controlling neural tissues includes a method for recording a patient defined on-off toggle from a motor action or sequence to set an operation mode of the processor control to one of active and standby. In some embodiments, the process control captures initiation triggers and contralateral stimulating parameters when the operation mode of the processor control is set to active. In some embodiments, the process control ignores initiation triggers and contralateral stimulating parameters when the operation mode of the processor control is set to standby. In some embodiments, the method for recording a patient defined on-off toggle from a motor action to set an operation mode of the processor control to one of active and standby includes receiving an initial patient defined motor action, recording initial neural activity corresponding to the initial patient defined motor action, storing the recorded initial neural activity, receiving a repeat patient defined motor action intended to copy the initial patient defined motor action, recording repeat neural activity corresponding to the repeat patient defined motor action, storing the recorded repeat neural activity, determining whether the recorded repeat neural activity matches the recorded initial neural activity, and storing, when the recorded repeat neural activity matches the recorded initial neural activity, the repeat neural activity in the micro processor to define the on-off toggle. In some embodiments, the method for recording a patient defined on-off toggle from a motor action to set an operation mode of the processor control to one of active and standby further includes returning to receive the repeat patient defined motor action intended to copy the initial patient defined motor action when the recorded repeat neural activity does not match the recorded initial neural activity. In this way, the patient can reliably perform motor actions to stimulate neural tissues when the patient intends to do so (i.e., in active mode), while ensuring that the same motor actions do not inadvertently trigger initiation of neural tissue stimulation when the patient does not intend to (i.e., in standby mode).

Pattern recognition processors capable of recording, storing and comparing previously recorded signals such that if a match within a defined tolerance is made it will trigger a predefined set of phased array electrodes stimulating areas near the contralateral damaged area.

Figure 2:
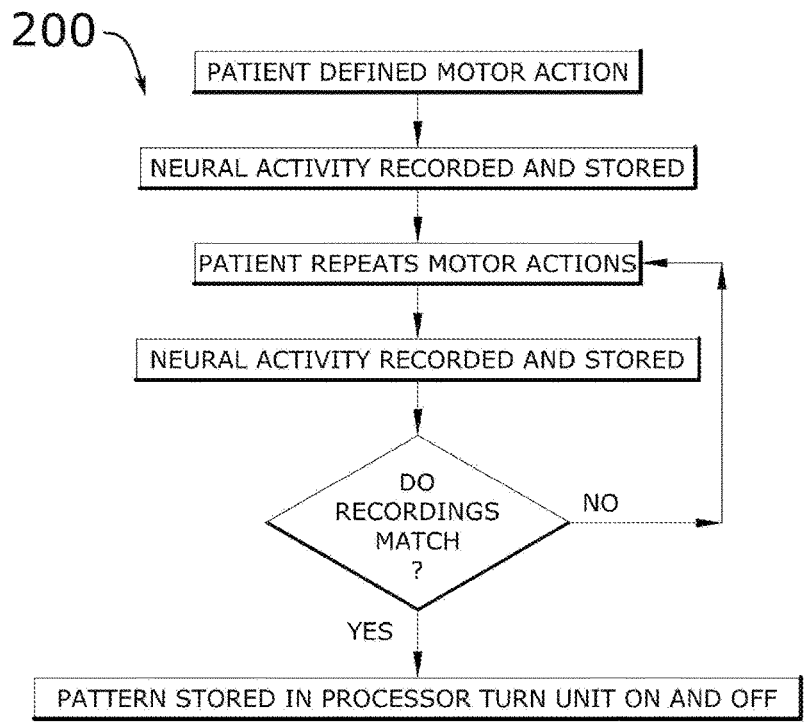
FIG. 2 conceptually illustrates a process for defining a motor action pattern by recording, storing, and comparing neural activity associated with a patient defined motor action in some embodiments.

By way of example, FIG. 2 conceptually illustrates a process for defining a motor action pattern by recording, storing, and comparing neural activity associated with a patient defined motor action 200. As shown in this figure, the process for defining a motor action pattern by recording, storing, and comparing neural activity associated with a patient defined motor action 200 includes patient defined motor action, followed by neural activity being recorded and stored. The patient then repeats the motor actions and the neural activity is again recorded and stored. In some embodiments, the process for defining a motor action pattern by recording, storing, and comparing neural activity associated with a patient defined motor action 200 then determines whether the recordings match or not. When the recordings match, the process for defining a motor action pattern by recording, storing, and comparing neural activity associated with a patient defined motor action 200 moves ahead to the next step in which the pattern stored in the processor turns the unit on and off. On the other hand, when the recordings do not match, the process for defining a motor action pattern by recording, storing, and comparing neural activity associated with a patient defined motor action 200 returns to the step in which the patient repeats the motor actions.

In some embodiments, the method for automatically controlling neural tissues includes a method for training a patient to perform a sequence of motor actions to trigger initiation of neural tissue stimulation. In some embodiments, the method for training a patient to perform a sequence of motor actions to trigger initiation of neural tissue stimulation includes receiving a first patient defined motor sequence, recording first motor sequence neural activity corresponding to the first patient defined motor sequence, storing the recorded first motor sequence neural activity, receiving a second patient defined motor sequence, recording second motor sequence neural activity corresponding to the second patient defined motor sequence, storing the recorded second motor sequence neural activity, initiating the first recorded motor sequence neural activity by the patient performing the first patient defined motor sequence at a higher rate of speed, initiating the second recorded motor sequence neural activity by the patient performing the second patient defined motor sequence at the higher rate of speed, and repeatedly increasing the rate of speed while initiating the first and the second recorded motor sequence neural activities by the patient performing the first and the second patient defined motor sequences, respectively. In this way, the patient can improve the accuracy and speed of performing the patient defined motor sequences to reliably trigger stimulation of the corresponding neural tissue areas of the brain.

Figure 3:
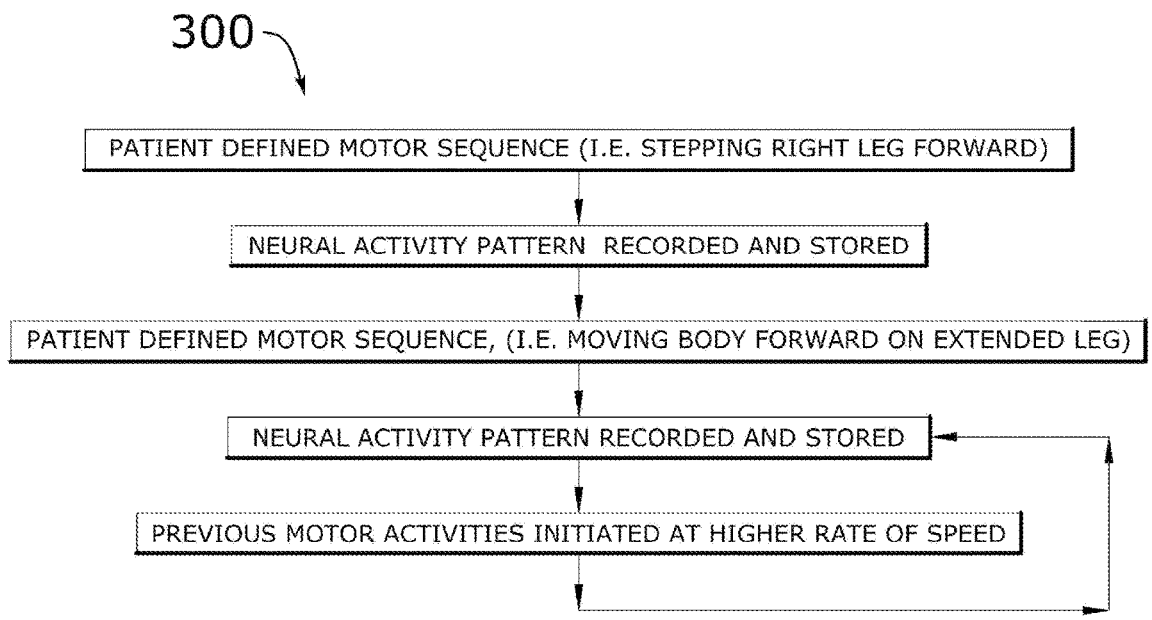
FIG. 3 conceptually illustrates a process for recording and storing neural activity patterns based on patient defined motor sequences in some embodiments.

Now turning to another example in which FIG. 3 conceptually illustrates a process for recording and storing neural activity patterns based on patient defined motor sequences 300. As shown in this figure, the process for recording and storing neural activity patterns based on patient defined motor sequences 300 includes a patient defined motor sequence. For example, the patient may step his or her right leg forward. Next, the process for recording and storing neural activity patterns based on patient defined motor sequences 300 moves to the next step in which neural activity pattern is recorded and stored. Then comes a patient defined motor sequence, such as moving the body forward on an extended leg. The process for recording and storing neural activity patterns based on patient defined motor sequences 300 continues with the neural activity pattern being recorded and stored. Then previous motor activities are initiated at higher rates of speed. In some embodiments, the process for recording and storing neural activity patterns based on patient defined motor sequences 300 returns to the step at which neural activity pattern is recorded and stored, and thereafter cycles steps until finished.

In some embodiments, the method for automatically controlling neural tissues includes a method for sending appropriate neural tissue stimulation to trigger a motor activity of a patient by monitoring and matching neural activity corresponding to a patient motor sequence to stored motor sequence neural activity that triggers stimulation of the appropriate neural tissue. In some embodiments, the method for sending appropriate neural tissue stimulation to trigger a motor activity of a patient by monitoring and matching neural activity corresponding to a patient motor sequence to stored motor sequence neural activity that triggers stimulation of the appropriate neural tissue includes monitoring neural activity in motor areas of the brain by the micro processor, identifying a previously recorded and stored motor sequence neural activity that matches the monitored neural activity, and sending an appropriate recorded neural tissue stimulation to the neural tissue area of the brain corresponding to the appropriate motor activity. In this way, the patient can affect motor movement sequences, which would normally correspond to neural tissue areas of the brain which have been damaged, by performing a compensating motor sequence defined to initiate stimulation of the neural tissue.

Figure 4:
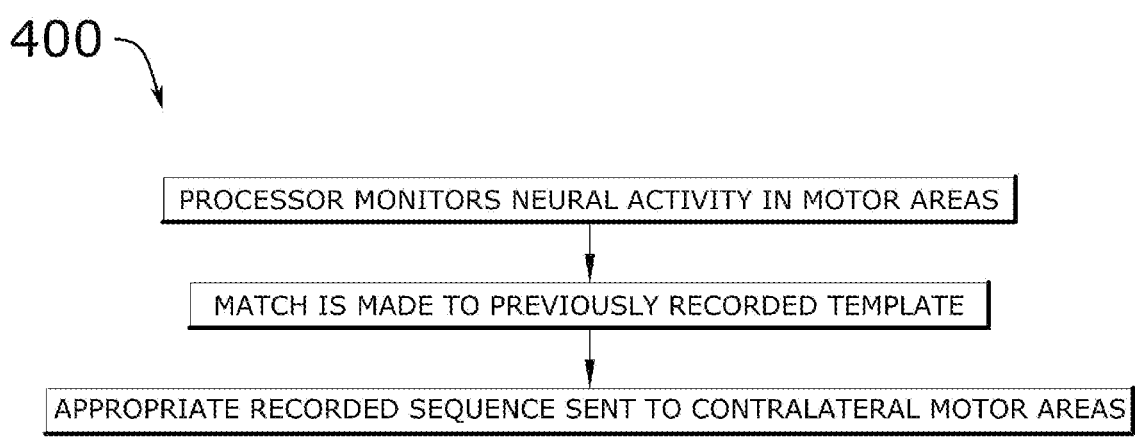
FIG. 4 conceptually illustrates a process for applying a neural activity recording to contralateral motor areas in some embodiments.

Another example is described next, by reference to FIG. 4, which conceptually illustrates a process for applying a neural activity recording to contralateral motor areas 400. In some embodiments, the process for applying a neural activity recording to contralateral motor areas 400 includes a step during which the processor monitors neural activity in motor areas. Next, a match is made to a previously recorded template. Following the match, the process for applying a neural activity recording to contralateral motor areas 400 includes a step during which an appropriate recorded sequence is sent to the contralateral motor areas.

To make the patient-initiated automatic neural tissue control system and methods of the present disclosure, the manufacturer of miniature implanted programmable stimulating devices is well defined. The electronic device required for this kind of neural control can be controlled externally or with radio frequency or magnetic field induction. Various electrodes and anchoring systems are also well defined in the art. Surgical implantation is also well documented.

A plurality of recording and stimulating points increase the ability of finer control and sequence activation.

Cross-modality neural stimulation is also possible. Auditory nerves could activate motor activity. Olfactory could be used to activate auditory or tactile. Artificially induced synesthesia or cross modality function.

To use the patient-initiated automatic neural tissue control system and methods of the present disclosure, once implanted the patient learns to control previously damaged areas by moving other areas that are not damaged. The patient could decide to use his swinging arm to swing his damaged leg forward. Bending his elbow for his knee and hand for his foot, allowing a bypass of damaged neural areas.

Additionally, this device could be used to restore or innervate many different sensory or motor functions.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 5:
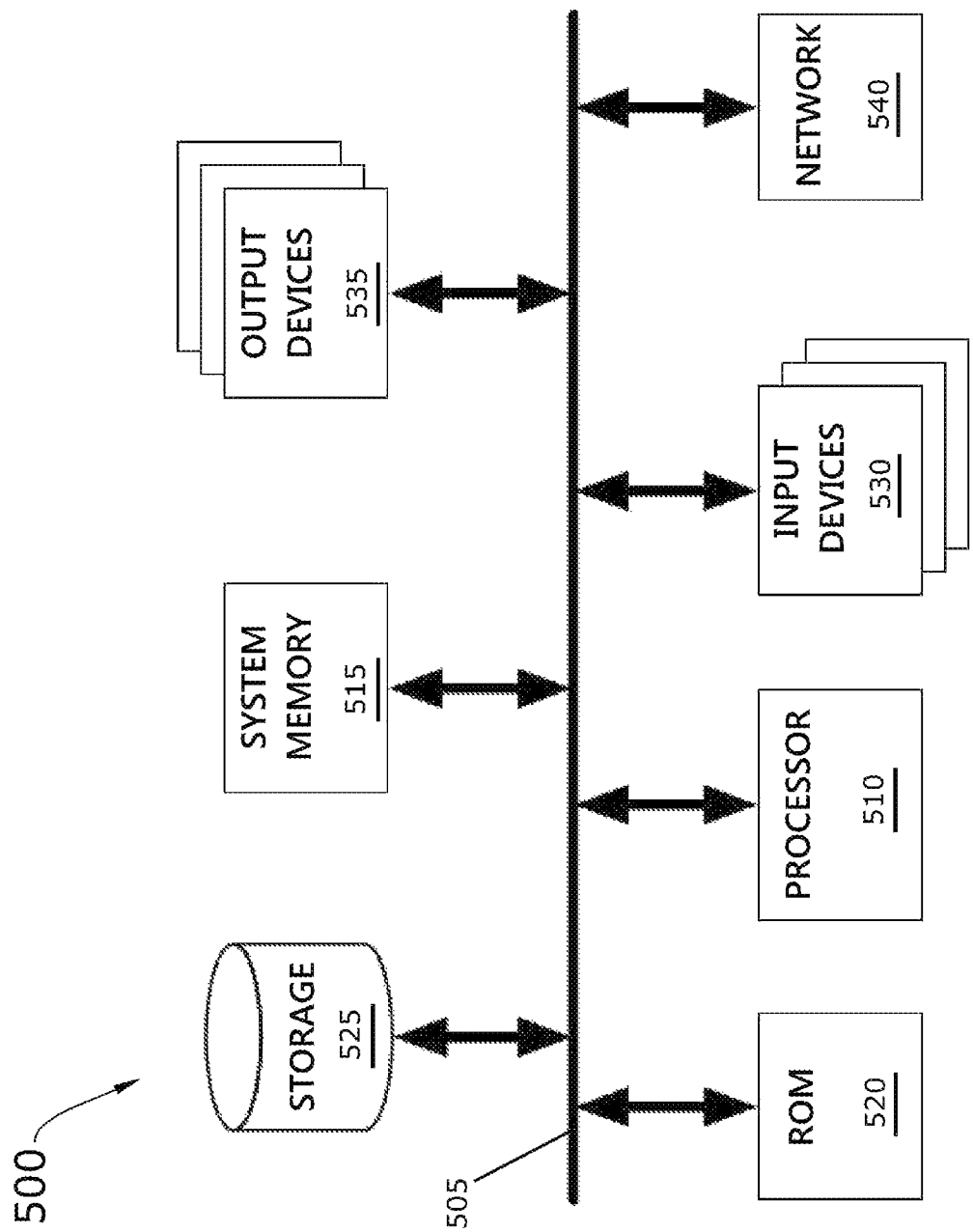
FIG. 5 conceptually illustrates an electronic system with which some embodiments of the invention are implemented.

FIG. 5 conceptually illustrates an electronic system 500 with which some embodiments of the invention are implemented. The electronic system 500 may be a computer, phone (cell phone, mobile phone, smartphone, etc.), PDA (iPod, other handheld computing device, etc.), or any other sort of electronic device or computing device. Such an electronic system includes various types of computer readable media and interfaces for various other types of computer readable media. Electronic system 500 includes a bus 505, processing unit(s) 510, a system memory 515, a read-only 520, a permanent storage device 525, input devices 530, output devices 535, and a network 540.

The bus 505 collectively represents all system, peripheral, and chipset buses that communicatively connect the numerous internal devices of the electronic system 500. For instance, the bus 505 communicatively connects the processing unit(s) 510 with the read-only 520, the system memory 515, and the permanent storage device 525.

From these various memory units, the processing unit(s) 510 retrieves instructions to execute and data to process in order to execute the processes of the invention. The processing unit(s) may be a single processor or a multi-core processor in different embodiments.

The read-only-memory (ROM) 520 stores static data and instructions that are needed by the processing unit(s) 510 and other modules of the electronic system. The permanent storage device 525, on the other hand, is a read-and-write memory device. This device is a non-volatile memory unit that stores instructions and data even when the electronic system 500 is off. Some embodiments of the invention use a mass-storage device (such as a magnetic or optical disk and its corresponding disk drive) as the permanent storage device 525.

Other embodiments use a removable storage device (such as a floppy disk or a flash drive) as the permanent storage device 525. Like the permanent storage device 525, the system memory 515 is a read-and-write memory device. However, unlike storage device 525, the system memory 515 is a volatile read-and-write memory, such as a random access memory. The system memory 515 stores some of the instructions and data that the processor needs at runtime. In some embodiments, the invention's processes are stored in the system memory 515, the permanent storage device 525, and/or the read-only 520. For example, the various memory units include instructions for processing appearance alterations of displayable characters in accordance with some embodiments. From these various memory units, the processing unit(s) 510 retrieves instructions to execute and data to process in order to execute the processes of some embodiments.

The bus 505 also connects to the input and output devices 530 and 535. The input devices enable the user to communicate information and select commands to the electronic system. The input devices 530 include alphanumeric keyboards and pointing devices (also called "cursor control devices"). The output devices 535 display images generated by the electronic system 500. The output devices 535 include printers and display devices, such as cathode ray tubes (CRT) or liquid crystal displays (LCD). Some embodiments include devices such as a touchscreen that functions as both input and output devices.

Finally, as shown in FIG. 5, bus 505 also couples electronic system 500 to a network 540 through a network adapter (not shown). In this manner, the computer can be a part of a network of computers (such as a local area network ("LAN"), a wide area network ("WAN"), or an intranet), or a network of networks (such as the Internet). Any or all components of electronic system 500 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIGS. 2-4 conceptually illustrate processes in which the specific operations of these processes may not be performed in the exact order shown and described. Specific operations may not be performed in one continuous series of operations, and different specific operations may be performed in different embodiments. Furthermore, the processes could be implemented using several sub-processes, or as part of a larger macro process. Thus, one of ordinary skill in the art would understand that the invention is not to be limited by the foregoing illustrative details, but rather is to be defined by the appended claims.

I claim:

1. A non-transitory computer readable medium storing a program which, when executed by a micro processor with an input-output (I/O) board and transceiver unit for transmission and reception of neural signals and which is part of a processor control device, automatically controls neural tissue in a brain of a patient, said program comprising sets of instructions for:

monitoring, by the micro processor, neural activity in motor areas of the brain received by the I/O board and transceiver unit from electrodes implanted near the motor areas of the brain;

searching a set of stored motor sequence neural activities that are templates of previously recorded motor sequence neural activities via electrodes in functioning areas of the brain;

identifying a stored motor sequence neural activity in the set of stored motor sequence neural activities that matches the monitored neural activity; and instructing the I/O board and transceiver unit to send an appropriate previously recorded neural tissue stimulation based on the identified stored motor sequence neural activity to electrodes near contralateral motor areas of the brain with neural tissue corresponding to a motor activity associated with the neural activity.

2. The non-transitory computer readable medium of claim 1, wherein the program further comprises sets of instructions for:

receiving, by the I/O board and transceiver unit, a first patient defined motor sequence;

recording, by the micro processor, a first motor sequence neural activity corresponding to the first patient defined motor sequence;

storing, by the micro processor, the recorded first motor sequence neural activity in the set of stored motor sequence neural activities as a first template of the first motor sequence neural activity;

receiving, by the I/O board and transceiver unit, a second patient defined motor sequence;

recording, by the micro processor, a second motor sequence neural activity corresponding to the second patient defined motor sequence; and storing, by the micro processor, the recorded second motor sequence neural activity in the set of stored motor sequence neural activities as a second template of the second motor sequence neural activity.

3. The non-transitory computer readable medium of claim 2, wherein the identified stored motor sequence neural activity that matches the monitored neural activity is a particular motor sequence neural activity comprising the first motor sequence neural activity and the second motor sequence neural activity.

4. The non-transitory computer readable medium of claim 3, wherein the program further comprises a set of instructions for repeatedly increasing a rate of speed for initiating.

* * * * *